United States Patent [19]
Snyder et al.

[11] Patent Number: 5,457,720
[45] Date of Patent: Oct. 10, 1995

[54] SYSTEM FOR KRYPTON-XENON CONCENTRATION, SEPARATION AND MEASUREMENT FOR RAPID DETECTION OF DEFECTIVE NUCLEAR FUEL BUNDLES

[75] Inventors: Dane T. Snyder, Byron; Raymond L. Armstrong, San Jose, both of Calif.

[73] Assignee: General Electric Company, Schenectady, N.Y.

[21] Appl. No.: 228,526

[22] Filed: Apr. 15, 1994

[51] Int. Cl.$^6$ .................................................. G21C 17/00
[52] U.S. Cl. ............................................ 376/253; 376/256
[58] Field of Search .................................. 376/253, 256, 376/249, 311; 250/370.03; 252/630; 55/66, 67, 208

[56] References Cited

U.S. PATENT DOCUMENTS

| | | | |
|---|---|---|---|
| 3,523,868 | 8/1970 | Dady | 376/253 |
| 3,680,284 | 8/1972 | Schmeling | 55/208 |
| 3,963,460 | 6/1976 | Stumpf et al. | 55/66 |
| 3,993,542 | 11/1976 | Blum et al. | 376/311 |
| 4,034,599 | 7/1977 | Osborne et al. | 73/40.7 |
| 4,226,675 | 10/1980 | Lewis et al. | 376/256 |
| 4,369,048 | 1/1983 | Pence | 55/66 |
| 4,435,644 | 3/1984 | Heki | 250/435 |
| 4,447,353 | 5/1984 | Pence et al. | 252/630 |
| 4,495,143 | 1/1985 | Gross et al. | 376/251 |

FOREIGN PATENT DOCUMENTS 898219  6/1992  United Kingdom.

*Primary Examiner*—Donald P. Walsh
*Assistant Examiner*—Meena Chelliah
*Attorney, Agent, or Firm*—James E. McGinness

[57] ABSTRACT

A process and system for the rapid concentration, separation and measurement of Kr-85 and Xe-133. By measuring the amount of Kr-85 radioisotope which is present, false positive signals for the vacuum sipping process can be eliminated. The fission gases are trapped by passing the recirculating gas stream through an adsorbing media. During this process, a known mixture of nonradioactive krypton and xenon is added to the gas stream which enters a thermal conductivity (TC) detector to calibrate the latter. The trapped gases are desorbed and injected into the inlet of a separating column. The column discharges into the TC detector. The TC detector discharge is diverted for counting to an evacuated beta detector chamber during the time that krypton is sensed by the TC detector. Any minute amount of Kr-85 is captured in the chamber, free of Xe-133. The detector discharge is diverted for counting to another evacuated beta detector chamber during the time that xenon is sensed by the TC detector. Any minute amount of Xe-133 is captured in the chamber, free of Kr-85.

20 Claims, 1 Drawing Sheet

SYSTEM FOR KRYPTON-XENON CONCENTRATION, SEPARATION AND MEASUREMENT FOR RAPID DETECTION OF DEFECTIVE NUCLEAR FUEL BUNDLES

FIELD OF THE INVENTION

This invention relates to a method and an apparatus for identifying defective fuel elements that are used in the core of a water-moderated nuclear reactor.

BACKGROUND OF THE INVENTION

The core of a nuclear reactor comprises a plurality of nuclear fuel bundle assemblies, each assembly consisting of a plurality of nuclear fuel rods. Each fuel rod comprises a circular cylindrical housing, i.e., cladding, which is sealed at both ends by respective end plugs. A plurality of nuclear fuel pellets are stacked in a vertical column inside the cladding to a height less than the length of the cladding, leaving a plenum space above the fuel column. A compression spring is placed inside the plenum for biasing the fuel pellets toward the bottom end plug of the fuel rod. A getter for removing contaminants from the interior atmosphere is conventionally installed inside the plenum.

The cladding serves two primary purposes: first, the cladding prevents contact and chemical reaction between the nuclear fuel and the coolant/moderator; and second, the cladding prevents the radioactive fission products, some of which are gases, from being released from the fuel rod into the coolant/moderator. Failure of the cladding, due to build-up of gas pressure or any other reason, could result in contamination of the coolant/moderator and associated systems by radioactive long-lived products to a degree which would interfere with plant operation.

A conventional technique for identifying defective fuel elements in water-moderated nuclear reactors is known as "fuel sipping". This technique identifies leaking fuel rods by obtaining and measuring fission gases that leak out of defective fuel rods. A known method and apparatus for performing fuel sipping is disclosed in U.S. Pat. No. 4,034,599, assigned to the present assignee, the disclosure of which is incorporated by reference herein. In accordance with this conventional technique, fuel sipping is accomplished by isolating a fuel bundle in a test chamber of purified water. The test chamber may be located either in the reactor vessel or at the bottom of the fuel pool. The test chamber contains an exhaust line near the top and a gas sparger at the bottom. Air is introduced into the test chamber through the gas sparger and is allowed to displace a portion of the water above the fuel element. This serves to form an air pocket above the fuel element, reduce the pressure in the test chamber and simultaneously purge the water surrounding the fuel element of fission gases pulled from defective fuel elements. The activity of fission gases entrained in the air are then measured by passing the air through a suitable radiation monitor. In a second step in the method, the pressure in the test chamber is further reduced to a vacuum, so as to increase the release of fission gases. In a third step of the method, the pressure in the test chamber is held at a vacuum and gas drawn from the air pocket above the fuel element for testing is recirculated so as to continuously purge released fission gases from the water surrounding the fuel element. In this manner, purge air and fission gas are trapped in the air pocket in the top of the test chamber and are removed for monitoring via a sample line. The radiation monitor in accordance with U.S. Pat. No. 4,034,599 is a gross beta detector. This detector simultaneously responds to both Kr-85 and Xe-133, which are the major fraction of the fission gases.

The measurement of fission gases is a key element of the fuel sipping process because of the easily achieved separation of gas and water. However, the Xe-133 isotope is a decay product of I-133, which is a water-soluble ion. This results in a background problem which is minimized by using demineralized make-up water. Demineralized condensate cannot be used because it often causes problems due to the release of Xe-133 from the decay of I-133 which has been carried over in the steam and exchanged on the condensate demineralizers. Pool water has large quantities of I-133 uniformly distributed therein. The concentration of I-133 is greatly increased when fuel pellet material escapes through a defect in the fuel rod cladding. These background problems must be considered when a "slow riser" is observed. In this case, a small increase in fission gas is indicated during the gas recirculation mode of a fuel sip. This increase could be due to a very small defect in a rod, pool water leaking into the test chamber, or desorption of gas from the oxide film which may also contain I-133 (chemically bound). This is a problem because it can lead to false identifications of a leaking fuel rod.

The Kr-85 isotope should not present this type of background problem because there are no water-soluble ionic species in its decay scheme. Therefore, once any species migrates from the inside to the outside of the fuel rod, it will separate and be swept away. It should be noted that Kr-85 is not as abundant as Xe-133. The only technique used to determine the quantity of Kr-85 in the presence of Xe-133 is to make repeated measurements to determine the decay characteristics of the mixture and calculate the respective quantities of Kr-85 and Xe-133 based on the decay half-lives. This measurement procedure can take months to complete. The rapid measurement of Kr-85 (exclusively) would reduce or eliminate a false positive response in the fuel sipping process.

SUMMARY OF THE INVENTION

The present invention is a unique process and system for the rapid concentration, separation and measurement of Kr-85 and Xe-133. By measuring the amount of Kr-85 radioisotope which is present, false positive signals for the vacuum sipping process can be eliminated. The invention utilizes chromatography to separate the radioisotopes to improve the resolution of spectrum analysis with low-resolution detectors.

The general process in accordance with the invention is as follows: (1) The fission gases are trapped by passing the recirculating gas stream through an adsorbing media. During this process, a known mixture of nonradioactive krypton and xenon is added to the gas stream which enters a thermal conductivity (TC) detector to calibrate the latter. (2) The trapped gases are desorbed and injected into the inlet of a separating column. The column discharges into the TC detector. (3) The TC detector discharge is diverted for counting to an evacuated beta detector chamber during the time that krypton is sensed by the TC detector. Any minute amount of Kr-85 is captured in the chamber, free of Xe-133. Alternatively, the TC detector discharge is diverted for counting to another evacuated beta detector chamber during the time that xenon is sensed by the TC detector. Any minute amount of Xe-133 is captured in the chamber, free of Kr-85.

The quantity of Kr-85 is the prime measurement because it must come from a defective rod within the test bundle, in accordance with the decay scheme of the fission gas constituents. Determining the ratio of Kr-85 to Xe-133 reduces the dependence on quantity, thereby eliminating pool water interference. Thus, this process may allow testing using pool water.

DETAILED DESCRIPTION OF THE PREFERRED EMBODIMENT

Figure 1:
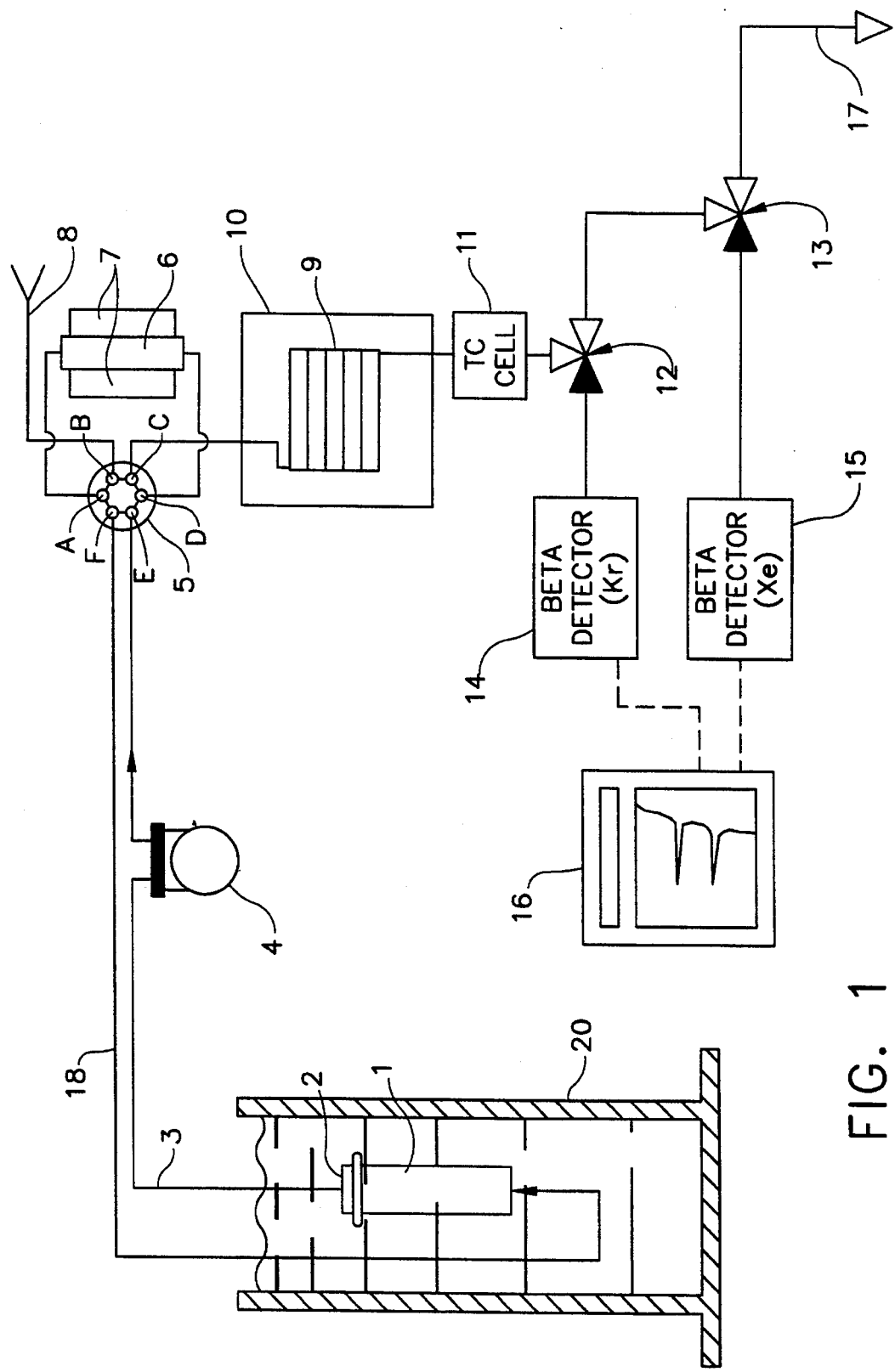
FIG. 1 is a block diagram showing the analytical system for concentrating, separating and measuring krypton and xenon in accordance with the preferred embodiment of the invention.

The analytical system of the invention can be used with any conventional sample chamber located in a fuel pool or in a reactor vessel. For the purpose of illustration, the analytical system will be described with reference to a sample chamber immersed in water contained in a fuel pool 20 (as shown in FIG. 1). The conventional sample chamber comprises a sipping can 1 and a sipping can head 2 mounted thereon. The sipping can 1 includes a gas sparger (not shown) disposed at the bottom thereof. The gas sparger serves to distribute purge air as a mass of bubbles. A return line 18 supplies air to the gas sparger. The sipping can head 2 is connected to a sample line 3. Purge air and fission gas are trapped in an air pocket inside the sipping can head 2 and are removed for monitoring through sample line 3.

The analytical system of the invention is located above the fuel pool or reactor vessel. In accordance with the preferred embodiment of the invention, a bellows pump 4 delivers the sample gas to port E of a six-port switching valve 5. Port D of switching valve 5 is connected to the inlet of a concentrator 6 via a first isolator valve (not shown).

Concentrator 6 comprises a gas chromatographic column containing a medium which, when subjected to a first temperature state, adsorbs different gases at different rates and retains the adsorbed gases. The retained gases are desorbed in response to a change from the first temperature state to a second temperature state. In accordance with the preferred embodiment, the medium is a burnt resin which has very high adsorption of krypton and xenon gases in the first temperature state (e.g., −30° C.) and which desorbs those same gases in the second temperature state (e.g., 200° C.).

Concentrator 6 is thermally coupled to a heater/cooler 7. The heater and cooler are alternately activated. The cooler can be activated to rapidly cool the concentrator to −30° C. by carbon dioxide expansion. The heater rapidly heats the cooled concentrator to 200° C. electrically.

The outlet of concentrator 6 is connected to port A of switching valve 5 via a second isolator valve (not shown). Completing the connections to switching valve 5, a source 8 of carrier gas (preferably nitrogen) is connected to port B; an inlet of a separator column 9 is connected to port C; and return line 18 is connected to port F.

The separator column 9 comprises a molecular sieve which adsorbs different gases at different rates, but has less capacity for retaining gases than the gas chromatographic column of concentrator 6 had. The result is that krypton and xenon gases will pass through the separator column at different rates, i.e., will exit the separator column at different times. The temperature inside the separator column is controlled by the column oven 10.

The outlet of separator column 9 is connected to the inlet of a thermal conductivity (TC) detector 11. The TC detector measures the thermal conductivity of the gaseous medium flowing therethrough. Thus, the thermal conductivity acquired by the TC detector will change over time as a function of the gas composition.

The outlet of TC detector 11 is connected to the inlet of a first two-way valve 12. Two-way valve 12 is used to direct sample flow to either a first beta detector 14 or to the inlet of a second two-way valve 13. Two-way valve 13 is used to direct sample flow to either a second beta detector 15 or to a vent 17.

The capacity of beta detector 15 is greater than that of beta detector 14. Beta detector 15 is intended to monitor the xenon radioisotope, which is more abundant in the fission gas than is the krypton radioisotope, while beta detector 14 is intended to monitor the krypton radioisotope. Both beta detectors are evacuated prior to beta detection. Each beta detector measures the number of beta particles emitted by the sample volume per minute, i.e., counts per minute (cpm), and outputs the data electronically. A conventional chart recorder 16 provides a written record of activity levels determined by the beta detectors 14 and 15.

Pump 4, switching valve 5, heater/cooler 7, two-way valves 12 and 13, and the isolation valves at the inlet and outlet of concentrator 6 may all be controlled by an electronic console (not shown), which can be remote to the gas processing unit. The basic process in accordance with the invention comprises a loading mode and an injection mode.

In the loading mode, the concentrator temperature is rapidly reduced to −30° C. or below by carbon dioxide expansion. Then radioactive krypton and xenon gases from the air pocket in sipping can head 2 are loaded into the concentrator 6 via ports D and E of switching valve 5. The radioactive krypton and xenon gases are adsorbed and retained in the cooled concentrator. The gases not adsorbed are recirculated to the sample chamber via ports A and F of switching valve 5 and via return line 18. As fission gas recirculates in the loop consisting of the sample chamber, sample line 3, concentrator 6 and return line 18, the concentration of krypton and xenon gases in the concentrator increases.

During the same loading sequence, a flow of carrier gas is supplied by source 8 to separator column 9 via ports B and C of switching valve 5. Then nonradioactive krypton and xenon gases are injected into the carrier gas and transported by the carrier gas to the separator column. The stable isotopes (nonradioactive) are used to check the separating characteristics of the system. The krypton and xenon gases are separated such that the krypton and xenon gases do not exit the separator column concurrently. In practice there is a definite time interval between the outflow of xenon and the outflow of krypton. These respective outflows then pass through the TC detector 11, which measures the thermal conductivities of the nonradioactive krypton and xenon respectively. The thermal conductivities of krypton and xenon appear as peaks at discrete times. These measured values are used to calibrate the TC detector, i.e., the nonradioactive isotopes tell where the radioactive isotopes should appear. Thereafter, the nonradioactive gases are exhausted via two-way valves 12 and 13 and vent 17.

When the desired concentration of radioactive krypton and xenon gases is attained in the concentrator, the gas processing system is switched from the loading mode to the injection mode. In the injection mode, the isolation valves at the inlet and outlet of concentrator 6 are closed while the heater raises the concentrator temperature to 200° C. or above by rapid electrical heating. At this temperature, the radioactive krypton and xenon gases are desorbed from the gas chromatographic column, but are held inside the concentrator until the isolator valves are opened and the concentrator is purged with carrier gas via ports B and A. The injected carrier gas transports the radioactive krypton and xenon gases into the separator column 9 via ports D and C of switching valve 5.

As the result of separation in separator column 9, the radioactive krypton and xenon gases are discharged into the TC detector 11 at different times. In the TC detector, the carrier gas serves as the reference. When the thermal conductivity measurement indicates the presence of krypton, the radioactive krypton gas discharged from the TC detector is diverted by two-way valve 12 to the evacuated beta detector 14. Any minute amount of Kr-85 radioisotope is captured in the chamber of beta detector 14, free of Xe-133 radioisotope. Similarly, when the thermal conductivity measurement indicates the presence of xenon, the radioactive xenon gas discharged from the TC detector is diverted by two-way valves 12 and 13 to the evacuated beta detector 15. This time any minute amount of Xe-133 radioisotope is captured in the chamber of beta detector 15, free of Kr-85 radioisotope. The respective counts per minute of krypton and xenon are recorded by chart recorder 16.

If the measured level of krypton exceeds the background level, then this is an indication that the nuclear fuel bundle tested may be defective. By measuring the level of KR-85 radioisotope, false positive signals for the vacuum process can be eliminated. Also, pool water interference can be eliminated by determining the ratio of Kr-85 to Xe-133.

The process of the invention was verified by testing. In this test a small amount of Xe-133 was diluted in air and processed. The TC detector discharge was collected in four gas sample bags and the contents of the bags were counted by a beta detector.. The first bag, taken when krypton was detected, had 520 counts per minute (cpm) above background. The next two bags, which were taken during the time period after the detection of krypton and before the detection of xenon, had 8 cpm and 3 cpm, respectively. The fourth bag, taken during xenon detection, had 710,000 cpm.

The TC detector signal and important system parameters are automatically recorded on a single chart recorder. In 10 minutes, this analyzer can process a sample and obtain the same information that normally takes weeks using the conventional method.

The preferred embodiment of the invention is designed either to be connected to the conventional fuel sipping system or to process cylinders of sample gas taken off-site. Depending on the gas sipping process and equipment used in conjunction therewith, the analytical system of the invention can be used to test individual fuel rods or selected fuel bundle assemblies.

The preferred embodiment of the invention has been disclosed for the purpose of illustration. Variations and modifications of the disclosed structure which do not depart from the concept of this invention will be readily apparent to engineers skilled in the art of gas processing. All such variations and modifications are intended to be encompassed by the claims set forth hereinafter.

We claim:

1. A system for analyzing the composition of fission gas, comprising:

means for separating a Kr-85 radioisotope from other components of said fission gas;

means for detecting the thermal conductivity of said separated Kr-85 radioisotope in a gaseous discharge exiting said separating means;

means for measuring the amount of Kr-85 radioisotope in a first volume; and means for diverting said separated Kr-85 radioisotope to said first volume.

2. The system as defined in claim 1, further comprising:

a gas chromatographic column for adsorbing Kr-85 radioisotope and other components of said fission gas in a first state and desorbing said Kr-85 radioisotope and said other components of said fission gas in a second state;

means for changing the state of said gas chromatographic column from said first state to said second state; and means for injecting said Kr-85 radioisotope and said other components of said fission gas into said separating means.

3. The system as defined in claim 1, wherein said separating means comprises a molecular sieve, and said measuring means comprises a beta detector.

4. The system as defined in claim 2, wherein said gas chromatographic column adsorbs at a first temperature and desorbs at a second temperature higher than said first temperature, and further comprising means for cooling said gas chromatographic column to said first temperature and means for heating said gas chromatographic medium to said second temperature.

5. The system as defined in claim 1, wherein said separating means further separates a Xe-133 radioisotope from other components of said fission gas, and said detecting means further detects said separated Xe-133 radioisotope in said gaseous discharge exiting said separating means, and further comprising:

means for measuring the amount of Xe-133 radioisotope in a second volume; and means for diverting said separated Xe-133 radioisotope to said second volume.

6. The system as defined in claim 2, further comprising isolation valve means having open and closed states, said isolation valve means in said closed state serving to isolate fission gas components desorbed in said gas chromatographic column and said isolation valve means in said open state releasing said desorbed fission gas components for injection into said separating means.

7. A method for analyzing the composition of fission gas having fission gas components, comprising the steps of:

concentrating said fission gas;

separating said fission gas components;

detecting the thermal conductivities of said fission gas components; and measuring the beta activity of a first radioactive gas component having a thermal conductivity corresponding to the thermal conductivity of a first known non-radioactive gas element.

8. The method as defined in claim 7, wherein said first radioactive gas component is the Kr-85 radioisotope.

9. The method as defined in claim 7, further comprising the steps of measuring the beta activity of a second radioactive gas component having a thermal conductivity corresponding to the thermal conductivity of a second known nonradioactive gas element and determining the ratio of said first radioactive gas component to said second radioactive gas component.

10. The method as defined in claim 9, wherein said first radioactive gas component is the Kr-85 radioisotope and said second radioactive gas component is the Xe-133 radioisotope.

11. The method as defined in claim 7, wherein said concentrating step comprises the step of adsorbing said fission gas components on a gas chromatographic medium, and further comprising the step of desorbing said fission gas components from said gas chromatographic medium after said concentrating step and before said separating step.

12. The method as defined in claim 11, wherein said gas chromatographic medium adsorbs at a first temperature and desorbs at a second temperature higher than said first temperature, said adsorbing step comprises the step of cooling said gas chromatographic medium to said first temperature and said desorbing step comprises the step of heating said gas chromatographic medium to said second temperature.

13. The method as defined in claim 7, wherein said separating step comprises the step of passing said fission gas components through an adsorptive medium having the characteristic of adsorbing said fission gas components and retaining said adsorbed fission gas components for different periods of time.

14. The method as defined in claim 7, further comprising the steps of supplying a calibration gas containing said first known nonradioactive gas element as a gas component, separating said calibration gas into 5 calibration gas components and detecting the thermal conductivity of said first known nonradioactive gas element before performing said step of separating said fission gas components.

15. A system for analyzing the composition of fission gas having fission gas components, comprising:

means for concentrating said fission gas;

means for separating said fission gas components;

means for detecting the thermal conductivities of said fission gas components; and first means for measuring the beta activity of a first radioactive gas component having a thermal conductivity corresponding to the thermal conductivity of a first known nonradioactive gas element.

16. The system as defined in claim 15, further comprising second means for measuring the beta activity of a second radioactive gas component having a thermal conductivity corresponding to the thermal conductivity of a second known nonradioactive gas element.

17. The system as defined in claim 15, wherein said concentrating means comprises a gas chromatographic medium which adsorbs at a first temperature and desorbs at a second temperature higher than said first temperature, and further comprising means for cooling said gas chromatographic medium to said first temperature and means for heating said gas chromatographic medium to said second temperature.

18. The system as defined in claim 15, wherein said separating means comprises an adsorbing medium which adsorbs and retains said fission gas components, the retention time being different for each respective fission gas component.

19. The system as defined in claim 16, further comprising means for diverting said first radioactive gas component discharged by said thermal conductivity detecting means to said first beta activity measuring means in response to detection of a thermal conductivity corresponding to the thermal conductivity of said first known nonradioactive gas element and diverting said second radioactive gas component discharged by said thermal conductivity detecting means to said second beta activity measuring means in response to detection of a thermal conductivity corresponding to the thermal conductivity of said second known nonradioactive gas element.

20. The system as defined in claim 19, further comprising means for supplying a calibration gas including said first and second known nonradioactive gas elements as gas components to said separating means while said fission gas is being concentrated in said concentrating means, wherein said separating means has the characteristic of separately discharging said first and second known nonradioactive gas elements to said thermal conductivity detecting means.

\* \* \* \* \*